United States Patent
MacEwen et al.

(10) Patent No.: US 10,900,959 B2
(45) Date of Patent: Jan. 26, 2021

(54) METHOD FOR QUANTITATIVELY MEASURING THE CONCENTRATION OF CHEMICALS IN AQUEOUS SOLUTION

(71) Applicant: SNF HC, Riceboro, GA (US)

(72) Inventors: Kimberley MacEwen, Richmond Hill, GA (US); Hisham El-Shaffey, Richmond Hill, GA (US); Michael Skriba, Richmond Hill, GA (US)

(73) Assignee: S.P.C.M. SA, Andrezieux-Boutheon (FR)

( * ) Notice: Subject to any disclaimer, the term of this patent is extended or adjusted under 35 U.S.C. 154(b) by 34 days.

(21) Appl. No.: 16/008,401

(22) Filed: Jun. 14, 2018

(65) Prior Publication Data

US 2019/0383803 A1    Dec. 19, 2019

(51) Int. Cl.
*G01N 33/52* (2006.01)
*G01N 33/53* (2006.01)
*G01N 33/24* (2006.01)
*G01N 33/543* (2006.01)

(52) U.S. Cl.
CPC ......... *G01N 33/5308* (2013.01); *G01N 33/24* (2013.01); *G01N 33/54386* (2013.01); *G01N 2430/60* (2013.01)

(58) Field of Classification Search
None
See application file for complete search history.

(56) References Cited

U.S. PATENT DOCUMENTS

| 5,593,850 A * | 1/1997 | Wetegrove | C07K 16/44 435/7.92 |
| 6,146,903 A | 11/2000 | Weatherbury et al. | |
| 6,197,522 B1 | 3/2001 | Keller et al. | |
| 2013/0280698 A1* | 10/2013 | Propper | G01N 33/5302 435/5 |
| 2015/0056719 A1 | 2/2015 | Karlovac et al. | |

FOREIGN PATENT DOCUMENTS

WO    WO2012057471 A2 *    5/2012    ............. A61B 5/145

OTHER PUBLICATIONS

Eltzov et al., Lateral Flow Immunoassays—from Paper Strip to Smartphone Technology, Electroanalysis 2015, 27, pp. 2116-2130. (Year: 2015).*

Barnett et al., An Inexpensive, Fast and Sensitive Quantitative Lateral Flow Magneto-Immunoassay for Total Prostate Specific Antigen, Biosensors, 2014, 4, pp. 204-220. (Year: 2014).*

Wehle et al., Master Thesis,Treatment of Polymer Containing Oilfied Water for Re-injection—Field Test with a Pilot Plant, OMV Exploration & Production GmbH, Sep. 2013, pp. 1-151. (Year: 2013).*

* cited by examiner

*Primary Examiner* — Gary Counts
(74) *Attorney, Agent, or Firm* — B. Aaron Schulman, Esq.; Stites & Harbison, PLLC

(57) ABSTRACT

The disclosure relates to a method for quantitatively measuring concentration in an aqueous solution of a water soluble polymer that is functionalized with at least one tracer, wherein the method involves impregnating a flow assay with a test area, introducing the flow assay into a test reader, and using the test reader to compare test data to a calibration curve so as to determine the concentration of the water-soluble polymer. This method allows the determination of residuals concentration in aqueous solution recovered from different industries, including oil and gas produced water, mining fluids, industrial water systems, and water treatment applications.

10 Claims, 4 Drawing Sheets

METHOD FOR QUANTITATIVELY MEASURING THE CONCENTRATION OF CHEMICALS IN AQUEOUS SOLUTION

FIELD OF THE INVENTION

The invention relates to the provision of a method for quantitatively measuring the concentration, in aqueous solution, of chemicals functionalized by a tracer.

The method of the invention allows the determination of residuals concentration in aqueous solution recovered from different industries, and especially oil and gas produced water, mining fluids, industrial water systems and water treatment applications.

BACKGROUND OF THE INVENTION

Industrial waters, oil and gas produced fluids, water treatment effluent, and mining fluids can contain residual chemicals which need to be quantified.

For example, water treatment implies the use of flocculants, which can be synthetic polymers. Municipal water standards often require the concentration of residual chemicals, such as the monomers used in synthetic polymers, to be monitored; especially in the case of potable water production.

In another example, Enhanced Oil Recovery, implies the use of viscosified aqueous fluids for oil flooding. Polymers are used to viscosify these aqueous fluids. In produced waters, polymer residuals need to be quantified to then recycle these fluids for another flooding operation. Knowing the concentration of polymer can allow for tailoring the treatment of these waters before recycling in the process.

Lateral flow assays (LFA) are generally used to develop a signal in the presence of a chosen tracer. Current lateral flow assays developed by Diagnostics Technologies (U.S. Pat. No. 6,146,903) and Rohm and Haas Company (U.S. Pat. No. 6,197,522) detect above or below specific thresholds. Through repeated testing, at several dilutions, residuals can be determined, semi-quantitatively at best. This method is tedious and yields results that are difficult to interpret.

For oil and gas, water treatment, mining and all applications implying the use of chemicals in aqueous solutions, there is a need for methods that quantitatively measure the concentration of these chemicals.

For oil and gas applications, to be used directly in the oil field, this method must be simple and use equipment which can be easily transported and handled in the field.

SUMMARY OF THE INVENTION

Given these considerations the applicant has developed a method for quantitatively measuring the concentration of chemicals functionalized with at least one tracer in aqueous solution A.

This method comprises at least the following successive steps:
a) Impregnating a flow assay containing at least one test area, that detects the tracer functionalizing the chemicals to be quantified, with solution A,
b) Introducing the flow assay into a test reader comprising at least the following elements:
  a set of control electronics,
  a signal capturing component,
  a radiation component,
  a housing component,
  a test tray which can hold at least a flow assay having a shape and a fixed position relative to the signal capturing component and the irradiation component,
c) Using the test reader by:
  Optionally exposing the flow assay to radiation to reveal signals of the tracer on the test area,
  Acquiring a digital image of said signals,
  Image processing for transforming said signals into test data
  Comparing said test data to a calibration curve
  determining concentration of the chemicals functionalized by at least one tracer in the aqueous solution.

Preferably, the signal capturing component is a digital image capturing component, the radiation is an electromagnetic radiation (for example light, illumination) and the test data corresponds to measured intensities of pixels of the digital image.

In another preferred embodiment, the signal capturing component is a magnetic intensity scanning component, the radiation is an alternating magnetic field and the test data is the count of the number of signals. For example, a magnetic intensity scanning component is a magnetometer composed of inductive sensor coils. For example, the alternating magnetic field is created using one or more electromagnetic coils.

Tracers used to functionalize chemicals whose concentration is quantified by the method of the invention can be monitored by colorimetry, fluorescence, luminescence, immunoassay or molecular biological techniques.

DETAILED DESCRIPTION OF THE INVENTION

Tracers that are visible may include those commonly described in the art such as dyes, pigments, and colorants. These compounds are often visible in either ambient or ultraviolet light. Suitable tracers useful with the present invention include but are not limited to those selected from the group consisting of Acridine Orange (CAS Registry No. 65-61-2); 2-anthracenesulfonic acid, sodium salt; Anthrasol Green IBA (CAS Registry No. 2538-84-3, aka Solubilized Vat Dye); bathophenanthrolinedisulfonic acid disodium salt (CAS Registry No. 52746-49-3); amino 2,5-benzene disulfonic acid: 2-(4-aminophenyl)-6-methylbenzothiazole; Brilliant Acid Yellow8G (CAS Registry No. 2391-30-2, aka Lissamine Yellow FF, Acid Yellow 7); Celestine Blue (CAS Registry No. 156290-9); cresyl violet acetate (CAS Registry No. 10510-54-0); dibenzofuransulfonic acid, 1-isomer (CAS Registry No. 42137-76-8); dibenzofuransulfonic acid, 2-isomer (CASUS 2006/014.4588 A1 Registry No. 257627-62-2); 1-ethylguinaldinium iodide (CAS Registry No. 606-53-3); fluorescein (CAS Registry No. 2321-07-5); fluorescein, sodium salt (CAS Registry No. 518-47-8, aka Acid Yellow 73, Uranine); Keyfluor White ST (CAS Registry No. 144470-484, aka Flu. Bright. 28); Keyfluor White CN (CAS Registry No. 16470-24-9); Leucophor BSB (CAS Registry No. 68444-86-0, aka Leucophor AP, Flu. Bright. 230); Leucophor BMB (CAS Registry No. 16470-24-9, aka Leucophor U. Flu. Bright. 290); Lucigenin (CAS Registry No. 2315-97-1, aka bis-N-methylacridiniumnitrate); mono-, di-, or tri-Sulfonated napthalenes, including but not limited to 1.5-naphthalenedisulfonic acid, disodium salt (hydrate) (CAS Registry No. 1655-29-4, aka1.5-NDSA hydrate); 2-amino-1-naphthalenesulfonic acid (CAS Registry No. 81-16-3); 5-amino-2-naphthaleneSulfonic acid, 4-amino-3-hydroxy-1-naphthalenesulfonicacid; 6-amino-4-hydroxy-2-naphthalenesulfonic acid; 7-amino-1,3-naphthalenedisulfonic acid, potassium salt; 4-amino-5-hydroxy-2,7-naphthalenedisulfonic acid; 5-dimethylamino-1-naphthalenesulfonic acid, 1-amino-4-naphthalene Sulfonic acid, 1-amino-7-naphthalene Sulfonic acid; and 2.6-naphthalenedicarboxylic acid, dipotassium salt; 3.4.9,10-perylenetetracarboxylic acid; Phorwite CL (CAS Registry No. 12270-53-0, aka Flu. Bright. 191); Phorwite BKL (CAS Registry No. 61968-72-7, aka Flu. Bright. 200); Phorwite BHC 766 (CAS Registry No. 52237-03-3); Pylaklor White S-15A (CAS Registry No. 6416-68-8); 1,3,6,8-pyrenetetrasulfonic acid, tetrasodium salt; pyramine, (CAS Registry No. 6358-69-6, aka 8-hydroxy-1,3,6-pyrenetrisulfonic acid, trisodium salt); quinoline (CAS Registry No. 91-22-5); Rhodalux (CAS Registry No. 550-82-3); Rhodamine WT (CAS Registry No. 37299-86-8); SafrainineO (CAS Registry No. 477-73-6); Sandoz CW (CAS Registry No. 56509-06-9, aka Flu. Bright, 235); Sandoz CD (CAS Registry No. 16470-24-9, aka Flu. Bright. 220); Sandoz TH-40 (CAS Registry No. 32694-95-4); Sulforhodamine B (CAS Registry No. 3520-42-1, aka Acid Red 52); Tinopal 5BM-GX (CAS Registry No. 169762-28-1); Tinopol DCS (CAS Registry No. 205265-334); Tinopal CBS-X (CAS Registry No. 27344-41-8); Tinopal RBS 200; Titan Yellow (CAS Registry No. 1829-00-1, aka Thiazole Yellow G), and any existing ammonium, potassium and sodium salts thereof. Other visible tracers useful with the present invention include fluoroscein (aka yellow/green dye) and rhodamine WTS (aka red dye).

Preferably, the tracer used in the method of the invention is a fluorescent group. Fluorescent tracers useful with the present invention include but are not limited to: fluorinated benzoic acids including 2-fluorobenzoic acid; 3-fluorobenzoic acid, 4-fluorobenzoic acid; 3,5-difluorobenzoic acid; 3,4-difluorobenzoic acid; 2,6-difluorobenzoic acid; 2,5-difluorobenzoic acid; 2,3-difluorobenzoic acid; 2,4-difluorobenzoic acid; pentafluorobenzoic acid; 2,3,4,5-tetrafluorobenzoic acid: 4-(trifluoro-methyl)benzoic acid; 2-(trifluoromethyl)benzoic acid; 3-(trifluoro-methyl)benzoic acid; 3,4,5-trifluorobenzoic acid; 2,4,5-trifluorobenzoicacid; 2,3,4-trifluorobenzoic acid; 2,3,5-trifluorobenzoic acid; 2,3,6-trifluorobenzoic acid; 2,4,6-trifluorobenzoic acid; and the like, perfluoromethylcyclopentane (PMCP), perfluoromethylcyclohexane (PMCH), perfluorodimethylcyclobutane (PDMCB), m-perfluorodimethylcyclohexane (m-PDMCH), o-perfluoro-dimethylcyclohexane (o-PDMCH), p-Perfluorodimethylcyclohexane (p-PDMCH), perfluorotrimethylcyclohexane (PTMCH), perfluoroethyl-cyclohexane (PECH), perfluoroisopropylcyclohexane (IPPCH), and the like.

If the chemical is a monomer or a polymer, monomer functionalized by a fluorescent tracer which may be used in the context of the invention may be chosen for example from monomers comprising styrene sulfonate and styrene sulfonic, 4-methoxy-N-(3-N',N'-dimethylaminopropyl) naphthalimide, vinyl benzyl chloride quaternary salt (4-MND-MAPNVBQ); 4-methoxy-N-(3-N',N'-dimethylaminopropyl) naphthalimide, allyl chloride quaternary salt (4-MNDMAPN-AQ); 4-methoxy-N-(3-N', N'-dimethylaminopropyl) naphthalimide, 2-hydroxy-3-allyloxypropyl quaternary salt (4-MNDMAPN-HAPQ); N-allyl-4-(2-N',N'-dimethylaminoethoxy)naphthalimide, methyl sulfate quaternary salt (4-NADMAENMSQ); 5-allyloxy-4'-carboxy-1,8 naphthoylene-1', 2'-benzimidazole (5-ACNB); and 6-vinylbenzyloxy-4'-carboxyl-1,8-naphthoylene-1', 2'-benzimidazole (6-VBCNB), 4-vinyl-benzyl-boronic acid or 4-vinyl-benzyl-boronic boronate (VBB), acryloylbenzene boronic acid or acryloylbenzene boronate, methacryloylbenzene boronic acid or methacryloylbenzene boronate, 3-aclylamodiphenyl boric acid or, 3-aclylamodiphenyl boronate, 3-mehtaclylamodiphenyl boric acid or, 3-mehtaclylamodiphenyl boronate, 1-vinylimidazole, units derived from 9-anthracene, 2-vinylinaphthalene, 1-vinylpyrene, 4-vinyl-9,10-diphenylanthracene, 3-vinylphenanthrene, and 9-vinylacridine, 5-allyloxy-4'-carboxy-1,8-naphthoylene-1', 2'-benzimidaxole, 6-vinyl-benzyloxy-4'-carboxy-1,8-naphthoylene-1',2'benzimidazole, 5-allyloxy-4'-carboxy-1,8-naphthoylene-1',2'-benzimidazole, 1-(substituted) naphthalene, 9-(substituted)anthracene, 2-(substituted) benzimidazole, 5-(substituted)fluorescein, 4-(substituted) coumarin and 3-(substituted)-6,7-dimethoxy-1-methl-2 (1H)-quinoxazolinone, 8-(3-vinylbenzyloxy)-1,3,6-pyrene trisulfonic acid, 8-(4-vinylbenzyloxy-1,3,6, pyrene trisulfonic acid, and 8-(allyloxy)-1,3,6-pyrene trisulfonic acid, as well as lanthanide, such as europium, complexes formed with sulfonated polymers.

Preferably, the tracer used in the method of the invention is a detectable group which can be identified by immunoassay or molecular biological techniques.

Immunological methods for detecting proteins, cells, DNA and RNA gene sequences, hormones, vitamins, drugs and mycotoxins etc. have been known for many years, and have been widely reported in the literature. These methods are based upon the specific binding between a detection molecule and its target analyte. Detection molecules typically take the form of antibodies or immunoglobins, but can also be affirmers, aptamers, oligonucleotides and peptide nucleic acids. For antibodies used in such methods an animal with an adaptive immune system, typically a member of the murine or leporine family, is immunized, either with an analyte or a protein-hapten conjugate. The antibodies produced by the animal are then harvested and used, in the form of an immunoassay, to detect the analyte. Alternatively, affirmers used as detection agents, small non-antibody binding proteins or peptides with specificity and sensitivity comparable to antibodies, are genetically engineered through recombinant techniques. Oligonucleotides and peptide nucleic acids represent another option. Through hybridization, single stranded nucleic acid sequences can selectively recognize and bind their complementary sequence. Aptamers are yet another option for analyte detection. Aptamers are oligonucleotides possessing binding properties comparable to antibodies, but with molecular recognition not based on Waton-Crick or Hoogsteen base pairing, they are typically generated via directed evolution. These methods are based on the specific interaction between the detection molecule and the analyte.

Tracer that can be used for immunoassay detection may be chosen for example from 1-(dimethylamino)-5-naphthalenesulfonic acid and its halides (dansyl); 2-dimethylaminoazobenzene-4-sulfonic acid and its halides (dabsyl); 2,4,6-trinitro-benzenesulfonic acid and its salts (TNT); 3-benzoylquinoline-2-carboxaldehyde; 3-(2-furfoyl)quinolone-2-carboxaldehyde; 2,4-dinitrofluorobenzene (Sanfer's reagent); and ninhydrin.

If the chemical is a polymer, any chain transfer agent useful in controlling molecular weight of a polymer can be used as a tracer. Examples include but are not limited to: mercaptans, phosphinates, phosphonates, sulfinic acids (such as phenylsulfinic acid and p-toluenesulfinic acid), and amine-thiols. Reversible addition-fragmentation chain transfer, RAFT, agents useful in controlling molecular weight, composition and structure of a polymer can also be used as tracers. Examples include but are not limited to: trithiocarbonates, 2-cyanobutanyl-2-yl 3,5-dimethyl-1H-pyrazole-1-carbodithioate, 2-(dodecylthiocarbonothioylthio)-2-methylpropionic acid N-hydroxysuccinimide ester, cyanomethyl (3,5-Dimethyl-1H-pyrazole)-carbodithioate, 4-((((2-carboxyethyl)thio)carbonothioyl)thio)-4-cyanopentanoic acid; dithiocarbonates, benzyl 1H-pyrrole-1-carbodithioate, cyanomethyl methyl(4-pyridyl)carbamodithioate, 1-succinimidyl-4-cyano-4-[N-methyl-N-(4-pyridyl)carbamothioylthio] pentanoate; dithiobenzoates, benzyl benzodithioate, 2-cyano-2-propyl 4-cyanobenzodithioate, 2-nitro-5-(2-propynyloxy)benzyl 4-cyano-4-(phenylcarbonothioylthio)pentanoate. Initiators or initiator fragments useful in initiating free radical addition polymerization can be used as a tracer. Examples include but not limited to: peroxyesters, such as t-butyl-perbenzoate and t-amylperoxybenzoate; dialkylperoxides, such as dicumylperoxide; diacylperoxides, such as benzoyl peroxide; hydroperoxides, such as cumene hydroperoxide; azo compounds, such as 2-phenylazo-4-methoxy-2,4-dimethyl-valeronitrile, 2,2'-azobis-2-methyl-N-phenyl-propionamidine dihydrochloride, 2,2'-azobis-2(N-(chlorophenyl)-2-methylpropionamidine) dihydrochloride, 2,2'-azobis(2-(5-methyl-2-imidazoline-2-yl)propane) dihydrochloride, and 2,2'-azobis(2-(2-imidazolin-2-yl)propane) dihydrochloride. Any monomers or macro monomers which contain a moiety large enough to be recognized by an antibody or similar can also be used as tracers. Examples include but not limited to: poly-alkylene-glycolated monomers, polyethyleneglycol mono(meth)acrylates, N-polyethyleneglycol acrylamide; alkylated monomers, N-isopropylacrylamide, N-(isobutoxymethyl)acrylamide; carbohydrate derivatized monomers, 3-O-acryloyl-1,2:5,6-bis-O-isopropylidene-D-glucofuranose, 6-O-Acryloyl-1,2:3,4-bis-O-(1-methylethylidene)-α-D-galactopyranose, 1,2:3,4-di-O-isopropylidene-6-O-methacryloyl-α-D-galactopyranose; fused-ring monomers N-allyl-4-((4S)-2-oxo-hexahydro-1H-thieno[3,4-d]imidazol-4-yl)butanamide, 3-(allyloxy)-10,13-dimethyl-17-(5-methylhexan-2-yl)-2,3,4,7,8,9,10,11,12,13,14,15,16,17-tetradecahydro-1H-cyclopenta[a]phenanthrene, 3-(allyloxy)-hexadecahydro-1H-cyclopenta[a]phenanthrene; heterocyclic or heterocyclic-derivatized monomers, 1-vinylimidazole, 2-vinylpyridine, N-vinylcarbazole, N-vinylindole, 2-Bromo-3-(5)hexenylthiophene.

Preferably, the tracer used in the method of the invention is a detectable group which can be identified by an organic or inorganic phosphorus tag. Specifically, moieties containing a C-P (carbon-phosphorus) bond can be identified via complexation with a transition metal to exhibit a colour change detectable on flow assay.

In another preferred embodiment, the tracer is a magnetic particle. Magnetic particles can be a bead or a nanoparticle. Magnetic beads are a multi-functional nanomaterial with optical and magnetic or paramagnetic properties. Advantageously, chemicals functionalized by magnetic beads can be detected by immunoassay techniques. The magnetic beads can be directly attached to the chemicals for which we intended to determine the concentration or can be part of the lateral flow assay.

The lateral flow assay (LFA) is a paper-based platform for the detection of analytes in complex mixtures, where the sample is placed on a test device and the results are displayed in test area within 5-30 min. The tracer will interact, in the test area of the LFA either by a covalent bond, an electrostatic bond, a chemical reaction, etc, in order to fix the chemicals comprising the tracer on the test area. Thus, the test area of the LFA comprises any elements which enable the fixation of the chemicals comprising the tracer.

The test area to detect the tracer on the flow assay can be for example a line or point.

For step a) of the method of the invention, a person skilled in the art will select a flow assay adapted to the tracer, used to functionalize the chemicals, to be detected in the solution with which the flow assay will be impregnated. The type of tracer will allow the determination of the kind of test area required and so the selection of the required flow assay.

Preferably, the chemical for which the concentration will be quantified by the method of the invention, is a water-soluble polymer. A "water-soluble polymer" is a polymer which gives a solution without insoluble particles when it is dissolved under agitation at 25° C. and with a 50 g/L concentration in water.

Advantageously, the water-soluble polymer is an acrylamide-base polymer.

Acrylamide based polymers are obtained by polymerization of acrylamide and other water-soluble monomers with an ethylenically unsaturated moiety selected from the following families:

Anionic monomers. They are advantageously selected in the groups comprising monomers with an acid carboxylic moiety (e: acrylic acid or methacrylic acid and their salts), monomers with a sulfonic acid moiety (ex: 2-acrylamido-2-methyl propane sulfonic acid (AMPS) and its salts).

Non-ionic monomers. They are advantageously selected in the group comprising methacrylamide, acrylamide derivatives likes N-alkylacrylamide, as for instance N,N-dimethylacrylamide or mehtylolacrylamide, vinylformamide, N-vinylpyridine, N-vinylpyrrolidone, hydroxyalkyl(meth)acrylates and (meth)acrylates with an alkoxy chain can also been used.

Cationic monomers. They are preferably selected in the groups comprising diallyldialkyl ammonium salts likes diallyldimethyl ammonium chloride (DADMAC) and dialkylaminoalkyl (meth)acrylates likes dimethylaminoethyl (meth)acrylate ((M)ADAME) and their acidified or quaternized forms by means known by the skill man of the art, and also dialkylaminoalkyl (meth)acrylamide and their acidified or quaternized forms likes the (meth)acrylamide propyl trimethyl ammonium chloride (((M)APTAC).

Zwitterionic monomers can also been used. Anionic and cationic charges are associated on one single monomer. Example of zwitterionic monomers: sulfobetains likes sulfopropyl dimethylammonium ethylmethacrylate, sulfopropyl dimethylammonium propylmethacrylamide or sulfopropyl 2-vinylpyridinium, phosphobetains likes phosphato ethyl trimethylammonium ethylmethacrylate and carboxybetains.

The test reader comprises at least the following elements:
a set of control electronics,
a signal capturing component,
a radiation component,
a housing component,
a test tray which can hold at least a flow assay having a shape and a fixed position relative to the signal capturing component and the irradiation component, When the signal capturing component is a digital image capturing component and the magnetic radiation is an electromagnetic radiation (light, illumination), the test reader can be based on the equipment used in the medical field (US 2015/0056719).

The set of control electronics of test reader according to the present invention comprises at least one processor and an associated memory suitable for storing a computer program product comprising software instructions, which when they are executed by a computer implement some or all the steps of the method according to the present invention Preferably for step b) of the method of the invention, the set of control electronics, the signal capturing component and the radiation component are operatively located in a mobile terminal, for example a smartphone or touch pad, engaged with the housing component. Preferably, the signal capturing component is a flash comprised into the mobile terminal.

Preferably the housing component is a test reader attachment which can be repeatedly attached or detached to a smartphone.

In a preferred embodiment, the signal capturing component is a flash light-emitting diode, that is a part of the digital image capturing component, illuminating the flow assay from the front side.

For example, for step c) of the method of the invention, the signal induced by the tracer on the test area is in the form of colored, or fluorescent dots.

Acquisition of the digital image consists in taking a picture which is then digitized by set of electronics of the equipment.

The set of control electronics allows the processing of the digital image pixel by pixel.

The comparison of the pixels intensities of the digital image obtained by the method of the invention to a calibration curve stored in the sets of electronics enables to determine the concentration of chemical functionalized by at least one tracer.

It is also possible to determine the concentration of chemical functionalized by at least one tracer by counting the number of signals which corresponds, when magnetic particles are used, to the magnetic intensity. The comparison of the magnetic intensity obtained by the method of the invention to a calibration curve stored in the sets of electronics enables to determine the concentration of chemical functionalized by at least one tracer.

The method of the invention can be used to determine the concentration of water-soluble polymers functionalized with a tracer in oil and gas, mining, industrial water systems and water treatment applications.

In oil and gas applications, water-soluble polymers are preferably acrylamide based polymers. These water-soluble polymers can be used for flooding operations in enhanced oil recovery. For example, the method of the invention can be used to quantitatively measure the concentration of residual polymer after treatment of produced water to facilitate recycling for another injection and flooding operation.

So, another aspect of the invention is a process to measure quantitatively the concentration of water soluble polymers in back produced water from flooding operations for enhanced oil recovery processes consisting of:
  injecting an aqueous solution of water soluble polymer functionalized by a tracer in an oil formation through an injection well,
  performing a flooding operation,
  collecting fluid from production well
  separating oil and back produced water
  measuring the concentration of water soluble polymer in back produced water by the method previously described.

In water treatment applications, an example of the use of the method of the invention is the measurement of residual monomer concentration in water following treatment operations which include a flocculation step utilizing synthetic water-soluble polymers.

The following examples are provided to illustrate the present invention. The examples are not intended to limit the scope of the invention.

BRIEF DESCRIPTION OF THE DRAWING FIGURES

EXAMPLES

Example 1: Calibration Curve

Figure 1:
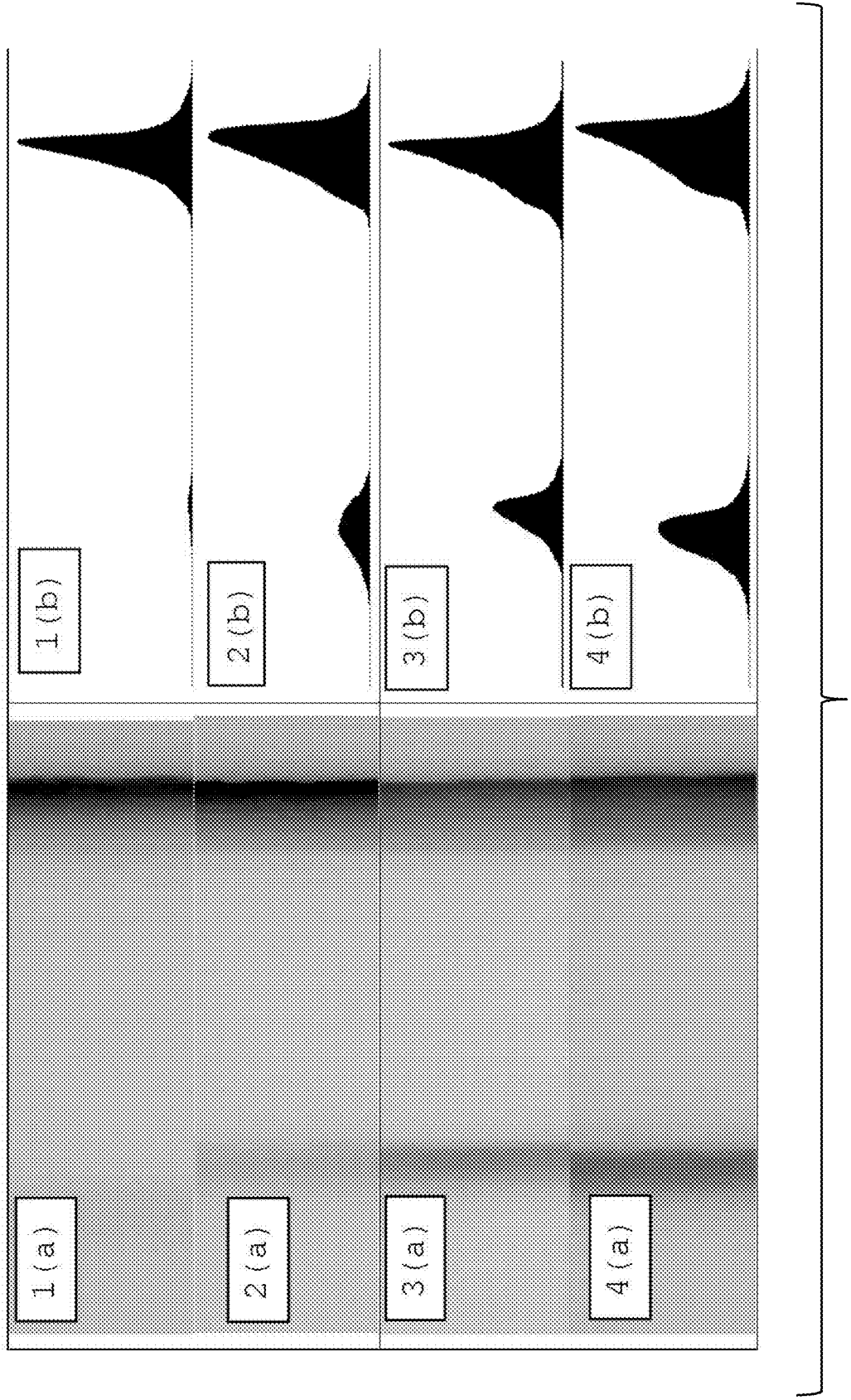
FIG. 1 represents representative digital images from the test reader for the calibration curve generation
Figure 2:
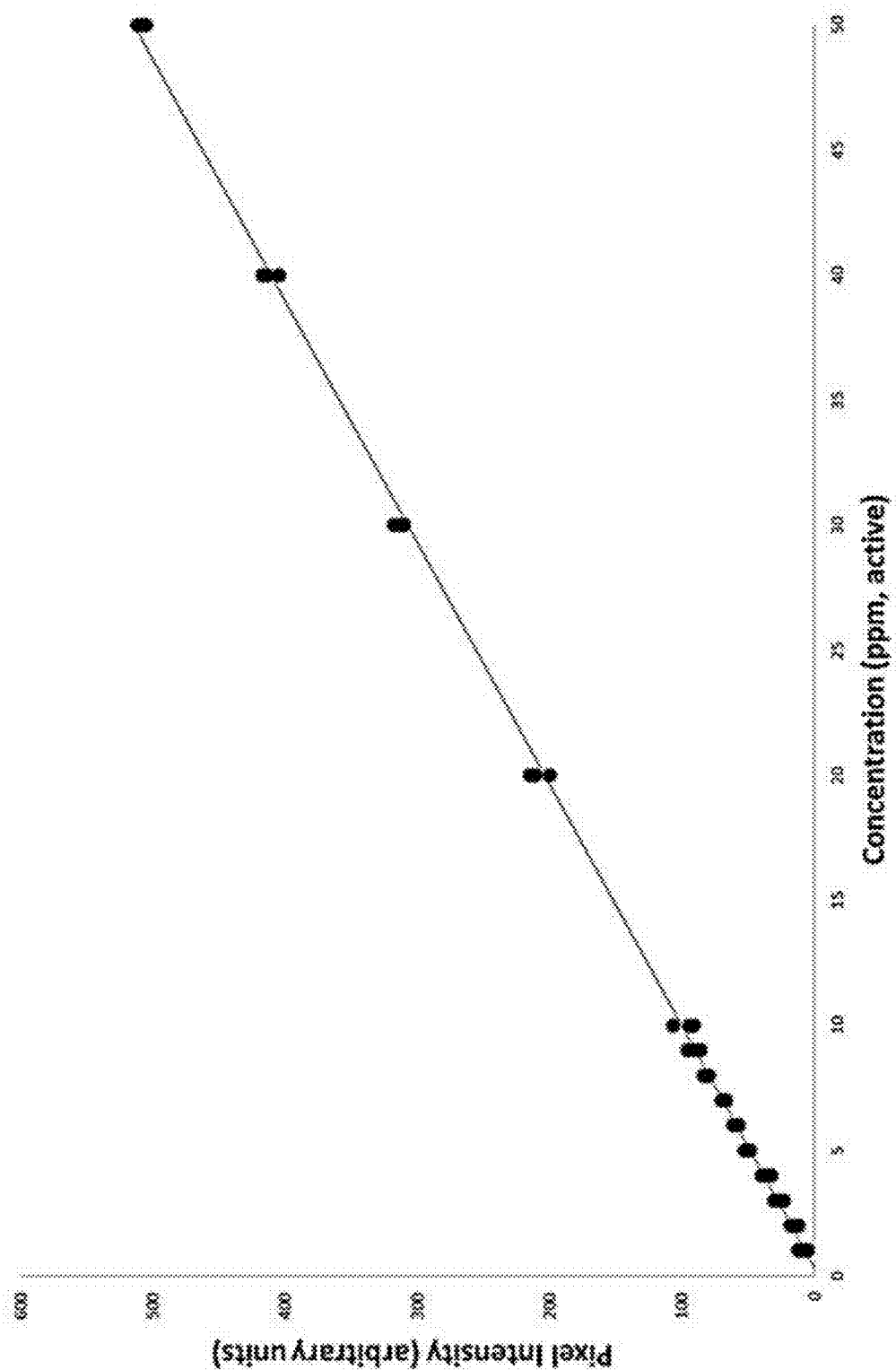
FIG. 2 represents the resulting calibration curve.

A series of known concentration standards was generated by up to 100,000 serial dilution from a mother solution of 10,000 ppm (active). Lateral Flow Assay (LFA's) were run for each of the 10 calibration standards and the resultant strip(s) was digitally imaged via a test reader. Some representative digital images from the test reader for the calibration curve generation are shown in FIG. 1. The resulting calibration curve is presented in FIG. 2 as a function of concentration.

Example 2: Adsorption Isotherm Sand Pack Preparation

Figure 3:
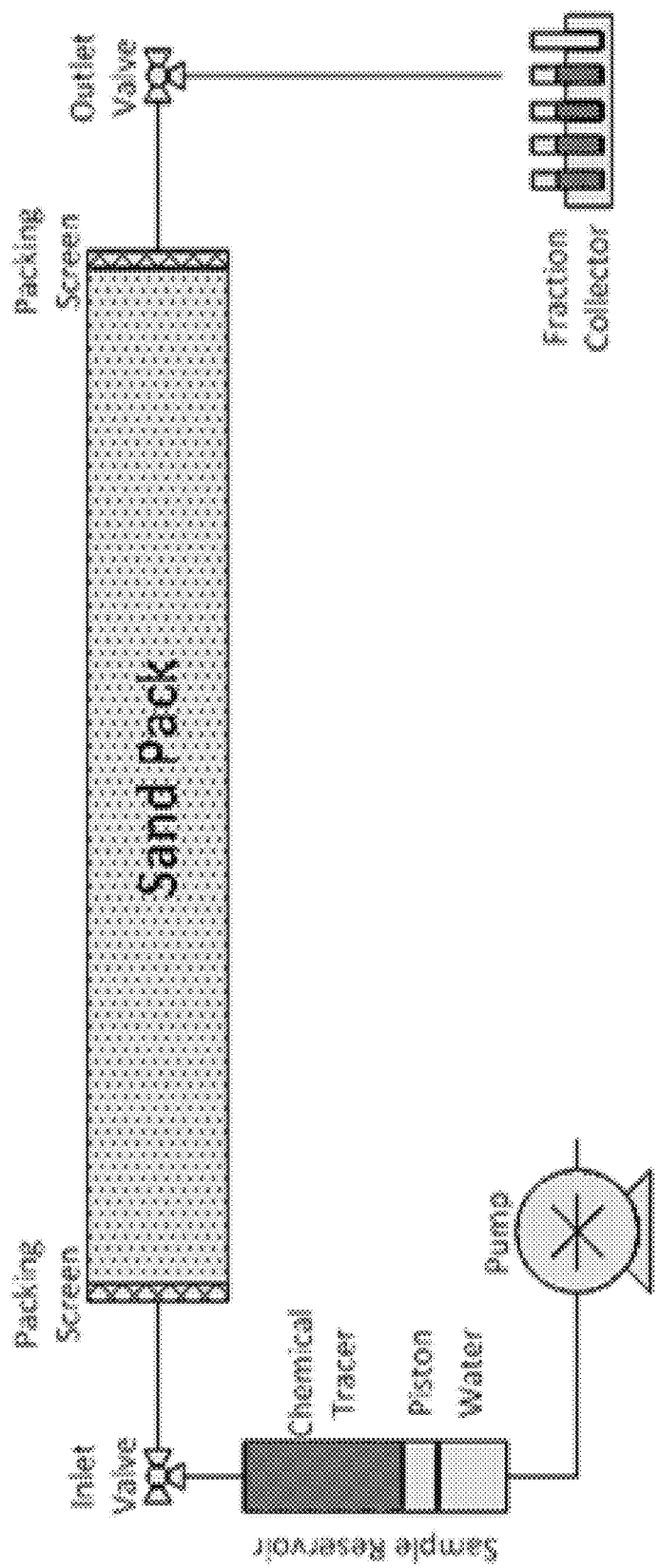
FIG. 3 represents a sand pack diagram.

A surrogate, unconsolidated sand pack was prepared to quantify chemical residuals. A representative sand pack diagram is shown in FIG. 3. Surrogate sand was packed into the column with packing screens on either end. Pore volume was determined using a salinity tracer test.

Permeability was calculated using Darcy's law, $$K = \frac{Q * \mu * L}{A * \Delta P} \qquad (1)$$

where K is the permeability in Darcy (D), Q is the flow rate (mL/sec), μ the viscosity (cPs), L is the length of the sand pack column (cm), A is the area of the sand pack column ($cm^2$), and $\Delta P$ is the pressure (Atm).

Example 3: Dynamic Sand Pack Flood for Residual Chemical Quantification

The chemical floods were carried out at ambient temperature using a flood sequence resembling a field squeeze process. A typical flood sequence includes:
  i) Injection of a spearhead solution
  ii) Injection of the chemical tracer concentration at ambient temperature until the effluent concentration reached the input level
  iii) Stop flow followed by a 24-hour shut-in
  iv) Post flush the sand pack with brine monitoring effluent chemical tracer concentrations Inhibitor Assay:

For comparison purposes, the chemical was functionalized in two ways to generate two separate species; one functionalized with a tracer for LFA analysis (Species 1: a hapten moiety coupled to a scale inhibitor) and the second functionalized with a fluorescent tracer (Species 2: a fluorescent moiety coupled to a scale inhibitor). Chemical tracer concentrations were quantified, for Species 1, using the method described in this patent and the fluorescent tracer Species 2 via fluorescence spectroscopy.

Figure 4:
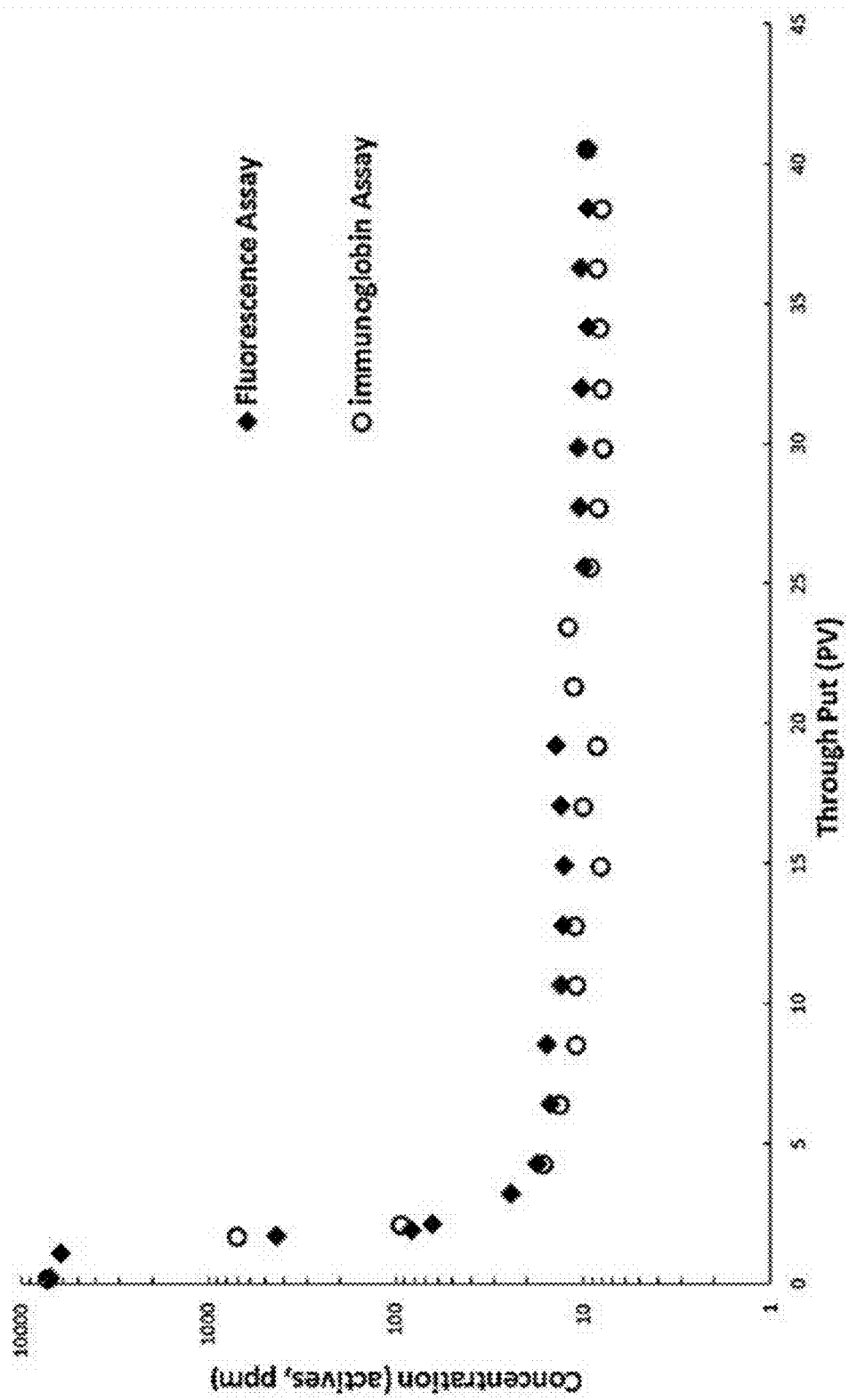
FIG. 4 represents the effluent concentration profiles, for Species 1 and Species 2, produced from the sand packs during the brine post flush.

Sand Pack Flood Chemical Tracer Returns:

The effluent concentration profiles, for Species 1 and Species 2, produced from the sand packs during the brine post flush, for both floods, are shown in FIG. 4. Both chemical species show a steep decline in their effluent concentrations during the early brine post flush. After that, the concentration declines slowly. Both effluent chemical Species 1 and 2 exhibit similar profiles. This demonstrates the efficacy of using a LFA reader to quantify chemical species residuals.

The invention claimed is:

1. A method for quantitatively determining concentration in an aqueous solution of a water-soluble polymer functionalized with at least one tracer, comprising:
   a) impregnating a flow assay containing at least one test area that detects the at least one tracer functionalizing the water-soluble polymer to be quantified, with the aqueous solution;
   b) introducing the flow assay into a test reader, said test reader comprising:
      a set of control electronics,
      a signal capturing component,
      a radiation component,
      a housing component, and
      a test tray which can hold at least a portion of the flow assay having a shape and a fixed position relative to the signal capturing component and the radiation component,
   c) using the test reader by:
      exposing the flow assay to radiation to reveal signals of the tracer on the test area,
      acquiring a digital image of said signals,
      image processing for transforming said signals into test data, and
      comparing said test data to a calibration curve in order to quantitatively determine concentration of the water-soluble polymer functionalized by at least one tracer in the aqueous solution,
   wherein the aqueous solution of the water soluble polymer is back produced water from a flooding operation for an enhanced oil recovery operation comprising water soluble polymers, and wherein said back produced water is obtained by:
      injecting an aqueous solution of water soluble polymer functionalized by a tracer in an oil formation through an injection well,
      performing a flooding operation,
      collecting fluid in a production well, and
      separating oil and back produced water.

2. The method according to claim 1 wherein the signal capturing component is a digital image capturing component, the radiation is an electromagnetic radiation and the test data corresponds to measured intensities of pixels of the digital image.

3. The method according to claim 1 wherein the signal capturing component is a magnetic intensity scanning component, the radiation is an alternating magnetic field and the test data is the count of the number of signals.

4. The method according to claim 2 wherein the tracer is a detectable group which can be identified by immunoassay or molecular biological techniques.

5. The method according to claim 2 wherein the tracer is a fluorescent group.

6. The method according to claim 2 wherein the tracer is an organic or inorganic phosphorus group.

7. The method according to claim 3 wherein the tracer is a magnetic particle.

8. The method according to claim 1 wherein the set of control electronics, the signal capturing component and the radiation component are operatively located in a mobile terminal engaged with the housing component.

9. The method according to claim 8 wherein the housing component is a test reader attachment which can be repeatedly attached or detached to a mobile terminal.

10. The method according to claim 2 wherein the signal capturing component is a flash light-emitting diode, that is a part of the digital image capturing component, illuminating the flow assay from the front side.

* * * * *